United States Patent
Buehler et al.

(10) Patent No.: US 10,966,458 B2
(45) Date of Patent: *Apr. 6, 2021

(54) AEROSOL GENERATING ARTICLE WITH A RUPTURING SYSTEM AND A BLISTER CAPSULE

(71) Applicant: Philip Morris Products S.A., Neuchatel (CH)

(72) Inventors: Frederic Ulysse Buehler, Neuchatel (CH); Rui Nuno Batista, Morges (CH)

(73) Assignee: Philip Morris Products S.A., Neuchatel (CH)

( * ) Notice: Subject to any disclaimer, the term of this patent is extended or adjusted under 35 U.S.C. 154(b) by 137 days.

This patent is subject to a terminal disclaimer.

(21) Appl. No.: 15/749,167

(22) PCT Filed: Aug. 8, 2016

(86) PCT No.: PCT/EP2016/068914
§ 371 (c)(1),
(2) Date: Jan. 31, 2018

(87) PCT Pub. No.: WO2017/029151
PCT Pub. Date: Feb. 23, 2017

(65) Prior Publication Data
US 2018/0228213 A1    Aug. 16, 2018

(30) Foreign Application Priority Data

Aug. 14, 2015    (EP) .................................... 15181169

(51) Int. Cl.
*A24F 47/00* (2020.01)
*A61M 15/00* (2006.01)

(52) U.S. Cl.
CPC ....... *A24F 47/002* (2013.01); *A61M 15/0035* (2014.02)

(58) Field of Classification Search
CPC ......... A24F 47/002; A24F 42/60; A24D 1/20; A61M 15/0035
(Continued)

(56) References Cited

U.S. PATENT DOCUMENTS 2,395,596 A * 2/1946 Vonnegut .................. A24F 3/02
131/223
2010/0313886 A1   12/2010 Wachtel et al.
(Continued)

FOREIGN PATENT DOCUMENTS

CN         101141892 A    3/2008
CN         101232825 A    7/2008
(Continued)

OTHER PUBLICATIONS

International Search Report and Written Opinion dated Oct. 21, 2016 in PCT/EP2016/068914 filed Aug. 8, 2016.
(Continued)

*Primary Examiner* — Eric Yaary
(74) *Attorney, Agent, or Firm* — Oblon, McClelland, Maier & Neustadt, L.L.P.

(57) ABSTRACT

There is provided an aerosol-generating article including at least one blister capsule including a volatile liquid, the article further including a rupturing system including a first tube and a second tube both arranged in operational engagement defining a volume; the first and second tubes being movable relative to each other along a first motion path from a first position to a second position, such that the defined volume is larger in the first position than in the second position; the first tube including a first rupturing member arranged at least partially inside the first tube, such that in the first position the first rupturing member is contained completely in the defined volume; and, in the second position, the first rupturing member at least partially protrudes (Continued)

from the defined volume and is configured to rupture the capsule and to form an aperture extending through the capsule.

15 Claims, 3 Drawing Sheets

(58) Field of Classification Search
USPC .......................................................... 131/273
See application file for complete search history.

(56) References Cited

U.S. PATENT DOCUMENTS

| | | | |
|---|---|---|---|
| 2011/0036363 A1* | 2/2011 | Urtsev | A24F 47/002 131/273 |
| 2012/0260928 A1* | 10/2012 | Herholdt | A24D 3/048 131/335 |
| 2016/0146506 A1 | 5/2016 | Brereton et al. | |

FOREIGN PATENT DOCUMENTS

| | | |
|---|---|---|
| CN | 102711532 A | 10/2012 |
| GB | 873410 | 7/1961 |
| JP | 60-33891 U | 3/1985 |
| JP | 2004-113023 A | 4/2004 |
| JP | 2017-520248 A | 7/2017 |
| RU | 2 470 680 C2 | 12/2012 |
| RU | 2012 131 270 A | 1/2014 |
| WO | WO 2004/112702 A2 | 12/2004 |
| WO | WO 2006/098171 A1 | 9/2006 |
| WO | WO 2007/090594 A1 | 8/2007 |
| WO | WO 2014/140087 A | 9/2014 |
| WO | 2014/207250 A1 | 12/2014 |
| WO | WO 2015/197502 A1 | 12/2015 |

OTHER PUBLICATIONS

Russian Office Action and Search Report dated Feb. 10, 2020, in Patent Application No. 2018108816, 18 pages (with English translation).

Combined Chinese Office Action and Search Report dated Apr. 27, 2020, in Patent Application No. 201680043605.6 (with English translation), 16 pages.

Office Action dated Sep. 10, 2020 in corresponding Japanese Patent Application No. 2018-506940 (with English Translation), 8 pages.

* cited by examiner

AEROSOL GENERATING ARTICLE WITH A RUPTURING SYSTEM AND A BLISTER CAPSULE

The present invention relates to an aerosol generating article comprising at least one blister capsule and a rupturing system.

Aerosol generating systems may comprise an aerosol generating article comprising a closed container with one or more aerosol generating agents including, for example, a flavourant such as menthol, or a nicotine containing substrate. To release the aerosol generating agent, the container needs to be broken or pierced, for example by inserting the aerosol generating article into an aerosol generating device. The combination of an aerosol generating article within an aerosol generating device may form an aerosol generating system. Typically, an aerosol generating article is not reusable. Typically, the aerosol generating device is reusable so that it can be used with multiple aerosol generating articles.

One known system described in WO-2014/140087-A1 comprises an aerosol generating device and an aerosol generating article comprising a container containing a nicotine solution and a delivery enhancing compound. The device comprises an elongate piercing member configured to pierce one or more compartments of the container when it is inserted into the device. Such a system requires precise engineering of the piercing member to ensure both compartments are properly pierced. This increases the manufacturing complexity and costs, together with the risk of the piercing member failing after multiple uses.

Therefore, it is an object of the present invention to provide a system for piercing or rupturing containers for an aerosol-generating system that is easy to operate and cost effective in production.

According to the present invention there is provided an aerosol-generating article comprising at least one blister capsule comprising a volatile liquid, the aerosol-generating article further comprising a rupturing system. The rupturing system comprises a first tube and a second tube, wherein the first tube and the second tube are arranged in operational engagement defining a volume. The first tube and the second tube are movable relative to each other along a first motion path from a first position to a second position, such that the defined volume is larger in the first position than in the second position. The first tube comprises a first rupturing member, arranged at least partially inside the first tube, such that in the first position, the first rupturing member is contained completely in the defined volume. In the second position, the first rupturing member at least partially protrudes from the defined volume to rupture the blister capsule to form an aperture extending through the blister capsule.

As used herein, the term "operational engagement" refers to the first tube and the second tube being coupled together and movable relative to each other. Preferably, the first tube and the second tube are arranged to slide relative to each other along the first motion path.

Aerosol generating articles according to the present invention advantageously enable the first rupturing member to engage with the at least one blister capsule only when the rupturing system is moved towards the second position. Therefore, a consumer has full control over when the at least one blister capsule is ruptured to release the volatile liquid.

Furthermore, since the first rupturing member is entirely contained within the volume defined by the first tube and the second tube when the rupturing system is in the first position, the article according to the present invention advantageously allows for easy handling, as, for example, no parts protrude from the rupturing system that may otherwise easily break off. It may also prevent injury to a consumer operating the article due to the enclosure of the rupturing member.

The first rupturing member preferably comprises a distal end comprising a rupturing portion and a proximal end, wherein the first rupturing member is coupled to the first tube at the proximal end such that during movement of the first tube along the first motion path, the rupturing portion describes a second motion path that is at least partially not parallel to the first motion path. The use of a second motion path that is non-parallel to the first motion path may advantageously facilitate movement of the rupturing portion away from the longitudinal axis of the first tube. This allows for a variety of different rupturing movements, such as a sideways cutting movement along the second motion path, for example.

The second motion path may be non-parallel to the first motion path so that an angle is defined between the first and second motion paths. The smallest angle between the first and second motion paths may be at least about 1 degree, preferably at least about 5 degrees, preferably at least about 10 degrees, preferably at least about 20 degrees. The smallest angle between the first and second motion paths may be about 90 degrees or less. The smallest angle between the first and second motion paths may be between about 60 degrees and about 90 degrees, preferably between about 70 degrees and about 90 degrees, preferably between about 80 degrees and about 90 degrees. Where at least one of the first and second motion paths comprises a curved portion, angles between the first and second motion paths are measured between tangents to the curved portion.

The second tube preferably comprises a guide member configured to guide the rupturing portion of the first rupturing member along the second motion path. The guide member may comprise a cam surface and the first rupturing member may comprise a cam follower surface, such that during relative movement of the first tube and the second tube from the first position to the second position along the first motion path, the cam follower surface of the first rupturing element engages with the cam surface of the guide member to guide the rupturing portion of the first rupturing member along the second motion path.

Preferably, the cam surface comprises a linear portion and an arc portion, and the cam follower preferably comprises a corresponding linear portion and arc portion. Providing a linear portion on the cam surface and cam follower enables the second motion path to allow the first rupturing member to pierce the blister capsule before the arc portions of the cam and cam follower engage. At the point at which the arc portions of the cam and cam follower engage, the relative motion introduces a progressive sideways movement along the second motion path to tear the blister capsule, therefore rupturing the blister capsule in a manner that allows air to flow through the blister capsule and the rupturing system.

The guide member may be coupled to the second tube at a proximal end of the guide member, and the guide member may be rotatable relative to the second tube about the proximal end. Providing such a guide member, configured to rotate and deflect away from a longitudinal axis of the rupturing system as the first tube and the second tube move along the first motion path, may enable an improved airflow through the rupturing system.

As used herein, the term "longitudinal" is used to describe the direction between a downstream or proximal end and an opposed upstream or distal end of the rupturing system. Each of the first and second tubes extends around the longitudinal axis. The term "transverse" is used to describe a direction perpendicular to the longitudinal direction.

In those embodiments in which the rupturing system comprises a guide member, preferably the at least one blister capsule comprises a first blister capsule and a second blister capsule, and preferably the guide member is a second rupturing member. The second rupturing member is preferably arranged at least partially inside the second tube, such that in the first position, the second rupturing member is contained completely in the defined volume of the first tube and the second tube. In the second position the first rupturing member at least partially protrudes from the defined volume to rupture the first blister capsule to form an aperture extending through the first blister capsule and the second rupturing member at least partially protrudes from the defined volume to rupture the second blister capsule to form an aperture extending through the second blister capsule.

In those embodiments comprising a second rupturing member, preferably the second rupturing member comprises a distal end comprising a rupturing portion and a proximal end, wherein the second rupturing member is connected to the second tube at the proximal end such that during movement of the second tube along the first motion path, the rupturing portion describes a third motion path that is at least partially not parallel to the first motion path. The third motion path may be similar to the second rupturing path, but mirrored along the longitudinal axis in embodiments in which the first rupturing portion and the second rupturing portion move in opposite directions. The third motion path may also facilitate movement of the second rupturing portion away from the longitudinal axis of the second tube. As described above with respect to motion of the first rupturing portion along the second motion path, movement of the second rupturing portion along the third motion path may allow for a variety of different rupturing movements, such as a sideways cutting movement along the third motion path, for example.

In any of the embodiments described above, and particularly those embodiments in which each rupturing portion is configured to move along an additional motion path that is non-parallel to the first motion path, each rupturing member is preferably coupled to the respective tube by a resilient member.

Preferably, each rupturing portion of each rupturing member has a wedge shaped longitudinal cross-section. One side of the wedge shape may be substantially parallel to the longitudinal axis of the rupturing system when the rupturing system is in the first position. In this way, the rupturing system may create an aperture within each blister capsule more effectively. In a preferred embodiment, each rupturing portion first pierces a blister capsule before the cam follower surface engages with the cam surface. As the rupturing system is moved from this intermediate position to the second position, the follower surface engages with the cam surface and provides for a transverse component of movement of the rupturing portion along the second motion path or the third motion path. The combination of the longitudinal and transverse movement of each rupturing portion breaks the respective blister capsule and widens the formed aperture to enable an airflow pathway to be formed when in use.

Preferably, each rupturing portion has a transverse cross-sectional shape such that a flow path is formed through the rupturing portion. For example, the transverse cross-sectional shape may be v-shaped, u-shaped, or the like. The rupturing portion may be at least partially hollow along its longitudinal length.

The first tube and the second tube are preferably substantially hollow, wherein an engagement surface of the first tube is configured to slide adjacent an engagement surface of the second tube. For example, an external surface of the first tube may be configured to slide under and adjacent an internal surface of the second tube. An internal surface of the first tube may be configured to slide over and adjacent an external surface of the second tube.

Preferably, the engagement surface of the first tube and the engagement surface of the second tube each comprise one or more resilient protrusions configured to cooperate to retain the system in the first position until a compressive force is applied to the rupturing system along the first motion path. Such resilient protrusions prevent accidental use of the article.

The resilient protrusions are preferably annular rings extending about the engagement surfaces of the first tube and the second tube. The annular rings preferably have a hemispherical cross-sectional shape.

The engagement surfaces of the first tube and the second tube may each comprise resilient protrusions configured to cooperate to retain the rupturing system in the second position. The resilient protrusions are preferably annular rings extending about the engagement surfaces of the first tube and the second tube. The annular rings preferably have a hemispherical cross-sectional shape.

In those embodiments in which an engagement surface of the first tube is configured to slide adjacent an engagement surface of the second tube, one of the first tube and the second tube preferably comprises a shoulder, the article further comprising a removable tab positioned adjacent the shoulder and between the first tube and second tube to prevent the first tube and second tube moving from the first position to the second position. For example, in embodiments in which an external surface of the first tube may be configured to slide under and adjacent an internal surface of the second tube, preferably the first tube comprises the shoulder and the removable tab is positioned between the shoulder and an end of the second tube. In embodiments in which an internal surface of the first tube may be configured to slide over and adjacent an external surface of the second tube, preferably the second tube comprises the shoulder and the removable tab is positioned between the shoulder and an end of the first tube.

A removable tab prevents use of the rupturing system even if a longitudinal force is applied to the first and second tubes. The removable tab is preferably coupled to at least one of the first tube and the second tube so that the removable tab is removable from the first tube and the second tube. The removable tab is preferably coupled using a plurality of frangible couplings. The removable tab may comprise a ring, free to rotate about the rupturing system and comprising a frangible portion to enable the ring to be separated from the rupturing system.

As will be appreciated, the removable tab is preferably removed prior to use of the article.

The second tube preferably comprises a first end and a second end, wherein the first tube overlaps the first end of the second tube in the first position, wherein at least one blister capsule is connected to the second end of the second tube, and wherein in the second position the first rupturing member ruptures the at least one blister capsule connected to the second end of the second tube. Providing the at least one blister capsule connected to the rupturing system can simplify the operation of the aerosol generating article by eliminating the need for a consumer to align a blister capsule with a separate In those embodiments in which the rupturing system comprises a second rupturing member, the at least one blister capsule connected to the second end of the second tube comprises a first blister capsule. The first tube preferably comprises a first end and a second end, wherein the second tube overlaps the first end of the first tube in the first position, wherein a second blister capsule is connected to the second end of the first tube, and wherein in the second position the second rupturing member ruptures the second blister capsule connected to the second end of the first tube.

The aerosol generating article may comprise a mouthpiece element adjacent to one of the first tube or second tube.

The aerosol generating article may comprise at least one heater configured to heat the volatile liquid within at least one blister capsule to form an aerosol.

The at least one blister capsule may comprise a blister shell, a tubular porous element disposed in the blister shell, a volatile liquid sorbed on the tubular porous element, and a film configured to seal the blister shell. The film and the blister shell are frangible so that, in the second position, each rupturing member at least partially protrudes from the defined volume to rupture the film and the blister shell of the respective blister capsule.

By providing such a blister capsule, a stable container for volatile liquid is provided, which may be manufactured easily, cost effectively, and at high volume, using standard manufacturing processes. In addition, each blister capsule enables a controlled volume of volatile liquid to be sorbed on a porous element for use in the aerosol-generating article.

The film for sealing the blister shell is preferably planar. The film for sealing the blister shell may not be planar, which may enable the volume of the sealed blister capsule to be increased.

A longitudinal axis of the tubular porous element may be aligned with a longitudinal axis of the blister shell. The shape outer dimensions of the cross-section perpendicular to the longitudinal axis of the tubular porous element may be substantially equal to the inner shape and dimensions of the cross-section perpendicular to the longitudinal axis of the blister shell. In this way, the tubular porous element is retained in position in the blister shell more easily.

The porous element is provided as a tubular element to enable an airflow pathway to be formed when the blister capsule is ruptured. For example, the tubular element enables a rupturing member to pierce both the blister shell and the sealing film without affecting the tubular porous element.

The tubular porous element may be made from any suitable absorbent plug or body, for example, a foamed metal or plastics material, polypropylene, terylene, nylon fibres or ceramic.

The blister shell preferably comprises a cavity and a flange extending around the periphery of the cavity. The tubular porous element is disposed in the cavity of the blister shell. The film is preferably sealed to the flange. The film may be sealed to the blister shell of the capsule using any suitable method, including: adhesive, such as an epoxy adhesive; heat sealing; ultrasonic welding; and laser welding.

The at least one blister capsule preferably has a substantially circular cross-section. A circular cross-section is particularly advantageous for reducing manufacturing complexity. However, any suitable cross-sectional shape may be used depending on the requirements of the capsule. For example, the cross-sectional shape may be triangular, rectangular, or elliptical. Preferably, each blister capsule has a cross-sectional shape that is substantially the same as the cross-sectional shape of the first tube and the second tube.

The blister capsule is preferably thin, that is to say, the depth of the blister shell is preferably less than the diameter of the blister shell.

The blister shell preferably has an internal diameter of between about 3 mm and about 15 mm, more preferably about 5 mm and about 10 mm.

The blister shell preferably has a depth, that is to say a longitudinal length, of between about 2 mm and about 12 mm, more preferably between about 3 mm and about 8 mm.

The tubular porous portion preferably has a longitudinal length substantially equal to the depth of the blister shell.

Preferably, the blister capsule is configured to hold between about 5 microlitres and about 50 microlitres of volatile liquid, more preferably between about 10 microlitres and about 30 microlitres of volatile liquid.

The at least one blister capsule may further comprise a further blister shell comprising a volatile liquid. The film is preferably further configured to seal the further blister shell. A further tubular porous element may be disposed in the further blister shell. Each blister shell may comprise a different volatile liquid. In embodiments comprising a blister shell and a further blister shell, the blister shell will be referred to as a first blister shell and the further blister shell will be referred to as a second blister shell.

The volume of the first blister shell and the volume of the second blister shell may be the same or different. The volume of the second blister shell is preferably greater than the volume of the first blister shell.

Each blister shell is preferably formed from a laminate material comprising at least two layers. Each layer may be formed from a metal film, preferably aluminium more preferably food grade, anodised aluminium, or a polymer such as polypropylene, polyurethane, polyethylene, fluorinated ethylene propylene. At least one layer of the laminate material may be paper or cardboard. The layers of the laminate may be bonded together using adhesive, heat, or pressure. When the laminate comprises a layer of aluminium and a layer of polymer material, the polymer material may be a coating. The coating layer may be thinner than the aluminium layer. The polymer layer material, and thickness, is preferably chosen in dependence on the composition of the volatile liquid to be contained. For example, the polymer layer is preferably chosen to reduce oxidation, and or reaction with the container, of the contained liquid. The laminate material may comprise more than two layers.

In those embodiments in which a first blister capsule is connected to a second end of the second tube and a second blister capsule is connected to a second end of the first tube, the volume defined by the first and second tubes may form a mixing chamber to facilitate mixing of the volatile liquids from both blister capsules after the blister capsules have been ruptured.

Preferably, each of the first and second blister capsules is press-fit into the second end of the respective tube. The at least one blister capsule may be connected to the respective tube using an adhesive, such as an epoxy-resin, or by heat sealing, ultrasonic welding or laser welding.

The first and second blister capsules may comprise the same or different volatile liquids.

The volatile liquid may comprise a nicotine-containing material, such as a tobacco-containing material comprising volatile tobacco flavour compounds which are released from the liquid upon heating. The liquid may comprise a non-tobacco material. The liquid may include water, solvents, ethanol, plant extracts and natural or artificial flavours.

Preferably, the liquid further comprises an aerosol former. Examples of suitable aerosol formers are glycerine and propylene glycol.

At least one blister capsule may comprise a source of nicotine. As such, the volatile liquid within at least one of the blister capsules preferably comprises one or more of nicotine, nicotine base, a nicotine salt, or a nicotine derivative.

The nicotine formulation may comprise natural nicotine or synthetic nicotine. The nicotine formulation may comprise nicotine base, a nicotine salt, such as nicotine-HCl, nicotine-bitartrate, or nicotine-tartrate, or a combination thereof.

The nicotine formulation may further comprise an electrolyte forming compound. The electrolyte forming compound may be selected from the group consisting of alkali metal hydroxides, alkali metal oxides, alkaline earth metal oxides, sodium hydroxide (NaOH), calcium hydroxide (Ca(OH)$_2$), potassium hydroxide (KOH) and combinations thereof.

The nicotine formulation may further comprise other components including, but not limited to, natural flavours, artificial flavours and antioxidants.

The liquid nicotine formulation may comprise pure nicotine, a solution of nicotine in an aqueous or non-aqueous solvent or a liquid tobacco extract.

The liquid nicotine solution may comprise an aqueous solution of nicotine base, a nicotine salt, such as nicotine-HCl, nicotine-bitartrate, or nicotine-tartrate and an electrolyte forming compound.

The nicotine formulation in the at least one blister capsule may be advantageously protected from exposure to oxygen (because oxygen cannot generally pass through the blister shell or sealing film) or from exposure to light, or from exposure to both light and oxygen, so that the risk of degradation of the nicotine formulation is significantly reduced. Therefore, a high level of hygiene can be maintained.

In those embodiments in which the article comprises more than one blister capsule, or in which the article comprises a blister capsule comprising two or more volatile liquids in two or more blister shells, at least one of the blister capsules or blister shells preferably comprises a volatile liquid delivery enhancing compound source. As used herein, by "volatile" it is meant the delivery enhancing compound has a vapour pressure of at least about 20 Pa. Unless otherwise stated, all vapour pressures referred to herein are vapour pressures at 25° C. measured in accordance with ASTM E1194-07.

Preferably, the volatile delivery enhancing compound has a vapour pressure of at least about 50 Pa, more preferably at least about 75 Pa, most preferably at least 100 Pa at 25° C.

Preferably, the volatile delivery enhancing compound has a vapour pressure of less than or equal to about 400 Pa, more preferably less than or equal to about 300 Pa, even more preferably less than or equal to about 275 Pa, most preferably less than or equal to about 250 Pa at 25° C.

The volatile delivery enhancing compound may have a vapour pressure of between about 20 Pa and about 400 Pa, more preferably between about 20 Pa and about 300 Pa, even more preferably between about 20 Pa and about 275 Pa, most preferably between about 20 Pa and about 250 Pa at 25° C.

The volatile delivery enhancing compound may have a vapour pressure of between about 50 Pa and about 400 Pa, more preferably between about 50 Pa and about 300 Pa, even more preferably between about 50 Pa and about 275 Pa, most preferably between about 50 Pa and about 250 Pa at 25° C.

The volatile delivery enhancing compound may have a vapour pressure of between about 75 Pa and about 400 Pa, more preferably between about 75 Pa and about 300 Pa, even more preferably between about 75 Pa and about 275 Pa, most preferably between about 75 Pa and about 250 Pa at 25° C.

The volatile delivery enhancing compound may have a vapour pressure of between about 100 Pa and about 400 Pa, more preferably between about 100 Pa and about 300 Pa, even more preferably between about 100 Pa and about 275 Pa, most preferably between about 100 Pa and about 250 Pa at 25° C.

The volatile delivery enhancing compound may comprise a single compound. The volatile delivery enhancing compound may comprise two or more different compounds.

In those embodiments in which the volatile delivery enhancing compound comprises two or more different compounds, the two or more different compounds in combination have a vapour pressure of at least about 20 Pa at 25° C.

The volatile delivery enhancing compound may comprise an aqueous solution of one or more compounds. Alternatively the volatile delivery enhancing compound may comprise a non-aqueous solution of one or more compounds.

The volatile delivery enhancing compound may comprise two or more different volatile compounds. For example, the volatile delivery enhancing compound may comprise a mixture of two or more different volatile liquid compounds.

The volatile delivery enhancing compound may comprise one or more non-volatile compounds and one or more volatile compounds. For example, the volatile delivery enhancing compound may comprise a solution of one or more non-volatile compounds in a volatile solvent or a mixture of one or more non-volatile liquid compounds and one or more volatile liquid compounds.

The delivery enhancing compound preferably comprises an acid or ammonium chloride. Preferably, the delivery enhancing compound comprises an acid. More preferably, the delivery enhancing compound comprises an acid having a vapour pressure of at least about 5 Pa at 20° C. Preferably, where the container or blister capsules comprises a nicotine-containing volatile liquid, the acid has a greater vapour pressure than the nicotine formulation at 20° C.

The delivery enhancing compound may comprise an organic acid or an inorganic acid. Preferably, the delivery enhancing compound comprises an organic acid. More preferably, the delivery enhancing compound comprises a carboxylic acid. Most preferably, the delivery enhancing compound comprises an alpha-keto or 2-oxo acid.

In a preferred embodiment, the delivery enhancing compound comprises an acid selected from the group consisting of 3-methyl-2-oxovaleric acid, pyruvic acid, 2-oxovaleric acid, 4-methyl-2-oxovaleric acid, 3-methyl-2-oxobutanoic acid, 2-oxooctanoic acid and combinations thereof. In a particularly preferred embodiment, the delivery enhancing compound comprises pyruvic acid or lactic acid.

In those embodiments in which each blister capsule comprises a tubular porous portion, each tubular porous portion is preferably a sorption element with an acid or ammonium chloride sorbed thereon.

As used herein, by "sorbed" it is meant that the volatile liquid is adsorbed on the surface of the sorption element, or absorbed in the sorption element, or both adsorbed on and absorbed in the sorption element.

The sorption element may be formed from any suitable material or combination of materials. For example, the sorption element may comprise one or more of glass, stainless steel, aluminium, polyethylene (PE), polypropylene, polyethylene terephthalate (PET), polybutylene terephthalate (PBT), polytetrafluoroethylene (PTFE), expanded polytetrafluoroethylene (ePTFE), and BAREX®.

The porous sorption element may comprise one or more porous materials selected from the group consisting of porous plastic materials, porous polymer fibres and porous glass fibres. The one or more porous materials may or may not be capillary materials.

Suitable porous fibrous materials include, but are not limited to: cellulose cotton fibres, cellulose acetate fibres and bonded polyolefin fibres, such as a mixture of polypropylene and polyethylene fibres.

The article may comprise one or more wrappers wrapped around at least a portion of at least one of the first and second tubes. For example, the article may comprise a first wrapper overlying at least a portion of the first tube, wherein the first wrapper is attached to the first tube. Providing a wrapper overlying at least a portion of the first tube and attached to the first tube can simulate the appearance of a more conventional smoking article. For example, the first wrapper can be configured to simulate the appearance of a tipping wrapper on a conventional smoking article.

Preferably, the first wrapper overlies substantially the entire outer surface of the first tube. Wrapping the first wrapper over the entire outer surface of the first tube may further facilitate the simulation of the appearance of a conventional smoking article, particularly in those embodiments in which the first wrapper is used to simulate a tipping wrapper.

One of the first and second tubes preferably comprises a shoulder configured to engage a first end of the other of the first and second tubes when the rupturing system is in the second position, wherein the shoulder and the first end are spaced apart to define an intermediate portion of the rupturing system between the shoulder and the first end, as described above.

In those embodiments in which one of the first and second tubes comprises a shoulder to define an intermediate portion of the rupturing system when the rupturing system is in the first position, the first wrapper may be arranged so that it does not overlap the intermediate portion. This arrangement may advantageously prevent damage to the first wrapper, such as folding, creasing or crumpling, when the first and second tubes are moved relative to each other into the second position.

In those embodiments in which the first wrapper does not overlap the intermediate portion, the article may further comprise a second wrapper overlying at least a portion of the second tube, wherein the second wrapper is attached to the second tube, and wherein the second wrapper does not overlap the intermediate portion. Providing a second wrapper overlying at least a portion of the second tube may further facilitate the simulation of the appearance of a conventional smoking article. For example, the second wrapper can simulate the appearance of a conventional cigarette paper that may be wrapped around a rod of tobacco in a conventional cigarette. Furthermore, arranging the second wrapper so that it does not overlap the intermediate portion may advantageously prevent damage to the second wrapper, such as folding, creasing or crumpling, when the first and second tubes are moved relative to each other into the second position.

Preferably, the second wrapper overlies substantially the entire outer surface of the second tube. Wrapping the second wrapper over the entire outer surface of the second tube may further facilitate the simulation of the appearance of a conventional smoking article, particularly in those embodiments in which the second wrapper is used to simulate a cigarette paper.

In those embodiments in which one of the first and second tubes comprises a shoulder to define an intermediate portion of the rupturing system when the rupturing system is in the first position, the first wrapper may alternatively at least partially overlap the intermediate portion, wherein the first wrapper is not attached to any part of the intermediate portion. Preferably, the first wrapper overlaps the entire intermediate portion. Wrapping the first wrapper over the intermediate portion may advantageously further facilitate the simulation of the appearance of a conventional smoking article by concealing the intermediate portion and providing the rupturing portion with a more uniform external appearance. Furthermore, arranging the first wrapper so that it is not attached to the intermediate portion may advantageously prevent damage to the first wrapper, such as folding, creasing or crumpling, when the first and second tubes are moved relative to each other into the second position. That is, the second tube may move underneath the portion of the first wrapper overlapping the intermediate portion when the first and second tubes are moved relative to each other from the first position into the second position.

In those embodiments in which the first wrapper overlaps the intermediate portion, the first wrapper may also overlap the second tube, wherein the first wrapper is not attached to any part of the second tube. Again, arranging the first wrapper so that it is not attached to the second tube may advantageously prevent damage to the first wrapper, such as folding, creasing or crumpling, when the first and second tubes are moved relative to each other into the second position.

In those embodiments in which the first wrapper overlaps a portion of the second tube, the article may further comprise a second wrapper overlying at least a portion of the second tube, wherein the second wrapper is attached to the second tube, and wherein a portion of the second wrapper underlies the portion of the first wrapper that at least partially overlaps the second tube so that the first wrapper and the second wrapper can move relative to each other when the rupturing system is moved from the first position to the second position. As described above, providing a second wrapper overlying at least a portion of the second tube may further facilitate the simulation of the appearance of a conventional smoking article. For example, the second wrapper can simulate the appearance of a conventional cigarette paper that may be wrapped around a rod of tobacco in a conventional cigarette. Furthermore, arranging the first and second wrappers so that they can move relative to each other when the rupturing system is moved from the first position to the second position can advantageously prevent damage to the first and second wrappers.

Preferably, the second wrapper overlies substantially the entire outer surface of the second tube. As described above, wrapping the second wrapper over the entire outer surface of the second tube may further facilitate the simulation of the appearance of a conventional smoking article, particularly in those embodiments in which the second wrapper is used to simulate a cigarette paper.

Each wrapper may be formed from a polymeric material, such as a polymeric film. Preferably, each wrapper is formed from a cellulosic material, such as paper.

In those embodiments in which the article comprises first and second wrappers, each of the first and second wrappers may be substantially the same colour. Preferably, the first and second wrappers are different colours.

In those embodiments in which the article comprises only a first wrapper overlying the first tube, the second tube may comprise a surface treatment applied to at least a portion of an outer surface of the second tube to further simulate the appearance of a conventional smoking article. For example, in those embodiments in which the first wrapper simulates a tipping wrapper, the second tube may comprise a surface treatment so that the outer surface of the second tube simulates the appearance of a conventional cigarette paper. For example, the surface treatment may impart a colour to the outer surface of the second tube. The colour may be white, such as a white ink. Additionally, or alternatively, the surface treatment may impart a texture to the outer surface of the second tube. The texture may be similar to the texture of a conventional cigarette paper.

It should be appreciated that particular combinations of the various features described and defined in any embodiments of the invention can be implemented and/or supplied and/or used independently or in combination.

The invention will be further described, by way of example only, with reference to the accompanying drawings in which.

Figure 1:
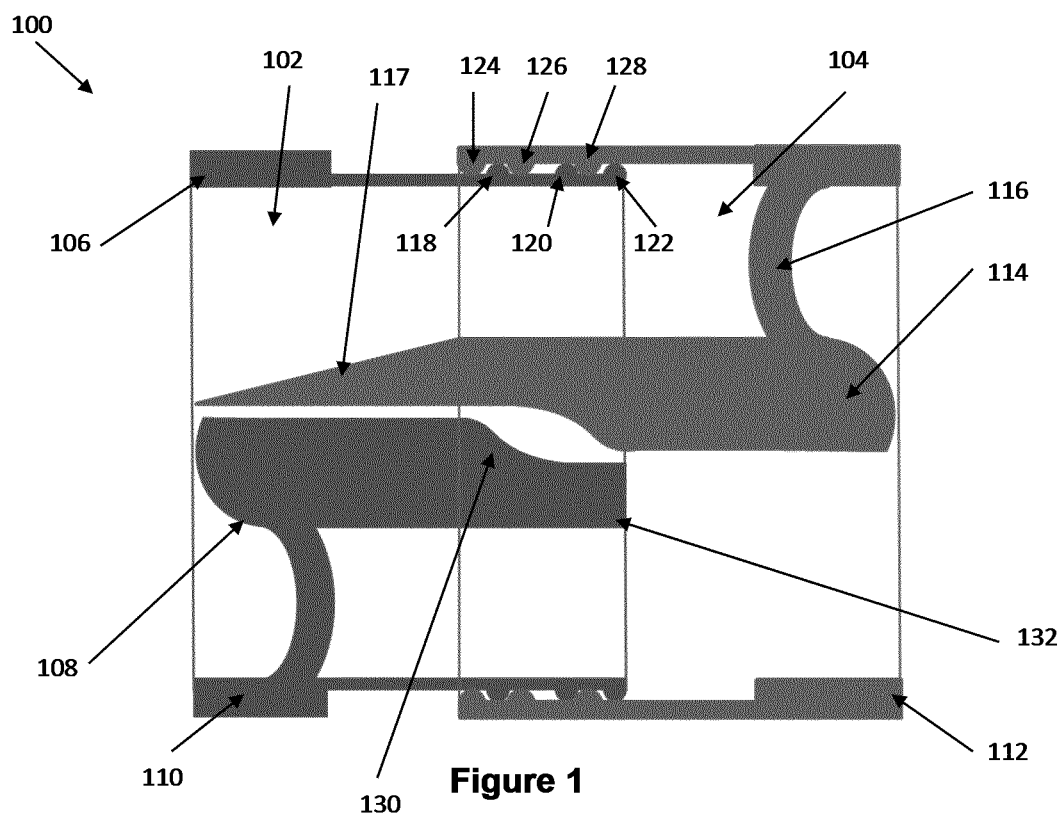
FIG. 1 shows a cross-sectional view of a rupturing system for forming part of an aerosol-generating article in accordance with the present invention.

FIG. 1 shows a cross-sectional view of a rupturing system 100 comprising a first tube 104 and a second tube 102. The first tube 104 comprises a hollow cylindrical portion 112 having a substantially circular cross-sectional shape, and a rupturing member 114 resiliently coupled to the hollow portion 112 by the resilient member 116. The rupturing member comprises a rupturing portion 117. The second tube 102 comprises a hollow cylindrical portion 106 having a substantially circular cross-sectional shape, and a guide member 108 resiliently coupled to the hollow portion 106 by the resilient member 110. The first tube 104 further comprises resilient protrusions 124, 126 and 128 and the second tube 102 further comprises resilient protrusions 118, 120 and 122.

As can be seen in FIG. 1, the second tube 102 is configured to partially slide within the first tube 104, such that they are in operational engagement, as described in detail below. The first tube and the second tube are configured to move along a first motion path. Such relative sliding of the first tube 104 and the second tube 102 engages a cam surface 130 of the guide member 108 with a cam follower surface 132 of the rupturing member 114, as described in detail below.

Figure 2:
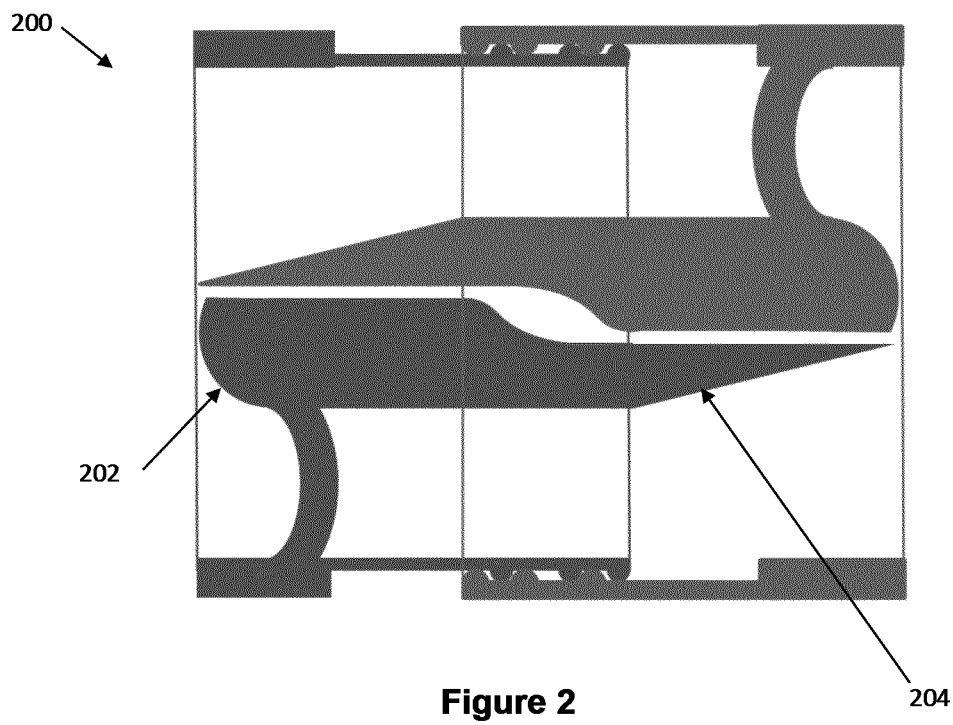
FIG. 2 shows a cross-sectional view of an alternative rupturing system for forming part of an aerosol-generating article in accordance with the present invention.

FIG. 2 shows an alternative rupturing system 200. As can be seen, the system 200 is similar to the system 100, and like reference numerals have been used to refer to like components. The second tube 102 of the system 200 comprises a guide member 202 having a rupturing portion 204. In this example, the guide member 202 is known as a second rupturing member.

Figure 3:
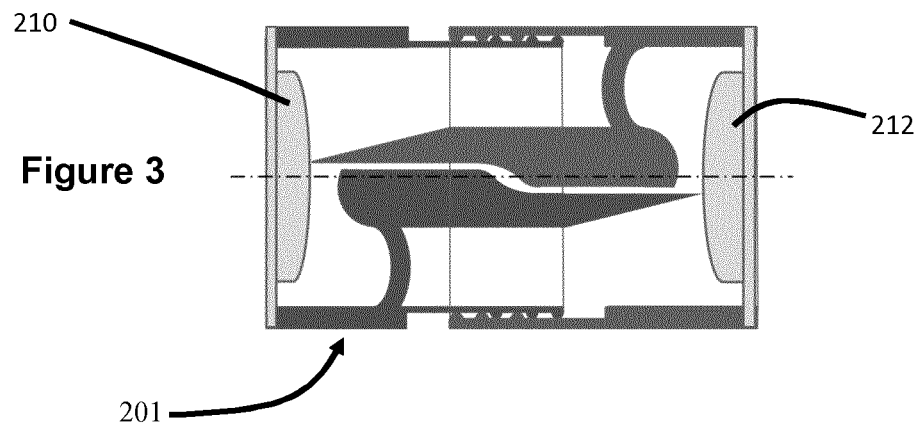
FIGS. 3, 4 and 5 show an aerosol-generating article according to the present invention and comprising the rupturing system of FIG. 2 moving from a first position to a second position.
Figure 4:
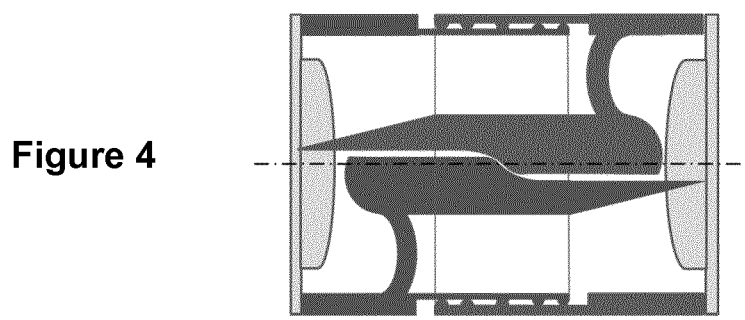
Figure 5:
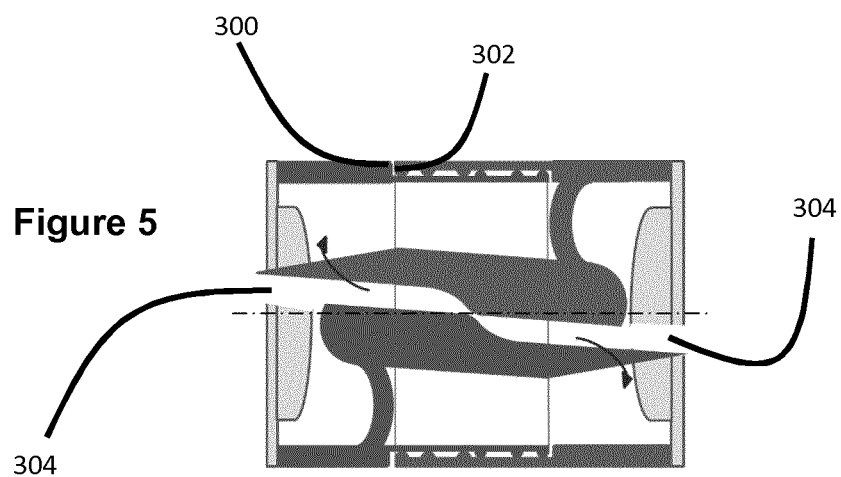

FIGS. 3 to 5 show an aerosol-generating article 201 comprising the rupturing system 200 of FIG. 2 in combination with first and second blister capsules 210, 212 connected to ends of the second and first tubes respectively. FIGS. 3 to 5 show the rupturing system 200 moving from a first position, FIG. 3, to an intermediate position, FIG. 4, to a second position FIG. 5, along the first motion path. As will be appreciated, the operation of the rupturing system 100 is substantially similar to that of system 200.

In FIG. 3 it can be seen that the protrusions 118, 120 and 122 of the second tube 102 cooperate with the protrusions 124, 126 and 128 of the first tube 104 to retain the first and second tubes in this first position until a longitudinal compressive force is applied to the system 200. Once sufficient force is applied, the second tube and the protrusions deform to allow the second tube to slide within the first tube, as shown in FIG. 4. As can also be seen in FIG. 4, the respective rupturing portions of the first tube and second tube begin to rupture the first and second blister capsules 210, 212 connected to ends of the second and first tubes respectively. At the same time, the cam surface 130 begins to engage with the cam follower surface 132. As the first tube and second tube are moved to the second position as shown in FIG. 5 the cam surfaces force the cam member 202 and the rupturing members to rotate about their respective resilient members 110 and 116. In doing so, the rupturing portions move in the transverse direction, and therefore the rupturing portions move along second and third motion paths that are not parallel to the first motion path.

Finally, as can be seen in FIG. 5, the resilient protrusions 118 and 128 cooperate to retain the system 200 in the second position. In addition, the first tube comprises a shoulder 300 which engages with an end face 302 of the second tube to prevent further relative sliding movement between the first and second tubes. The rupturing members have pierced entirely through the respective blister capsules 210, 212 to form an aperture 304 through each blister capsule. The lateral motion of the rupturing portions in the transverse direction widens each aperture 304 to form an airflow path through the rupturing system 200 and between the apertures 304 in the blister capsules 210, 212.

Figure 6:
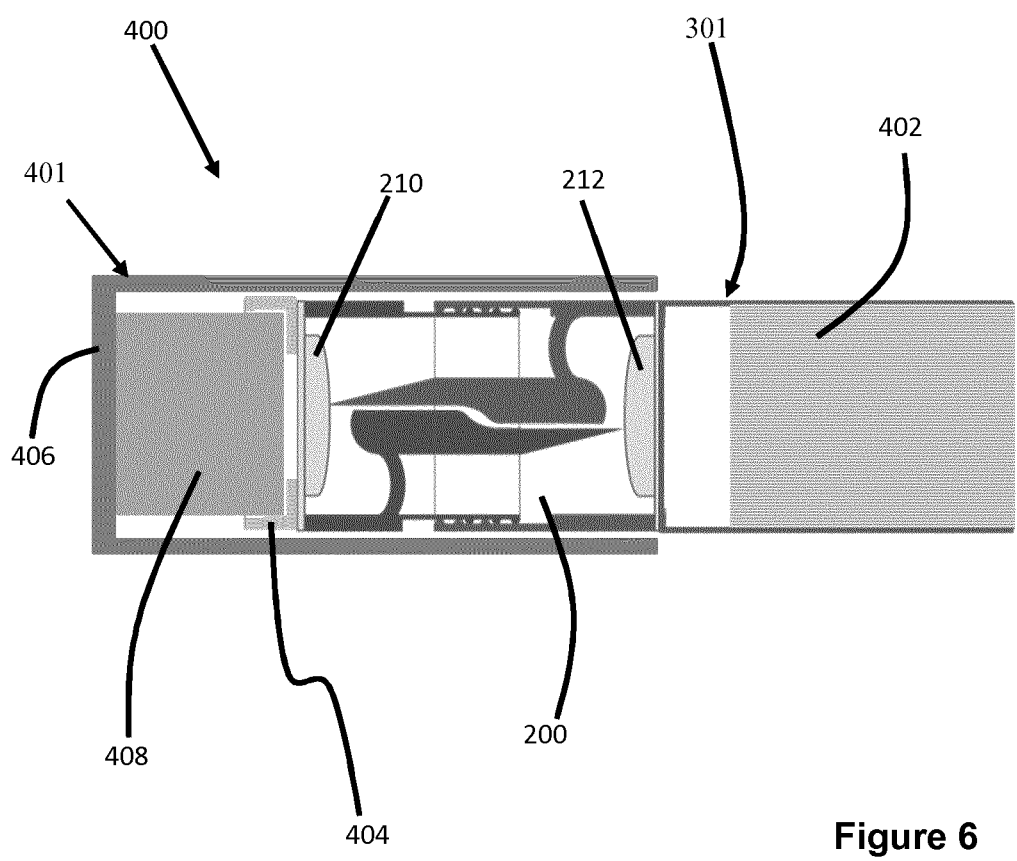
FIG. 6 shows a cross-sectional view of an aerosol-generating system comprising the aerosol-generating article of FIG. 3.

FIG. 6 shows a cross-sectional view of an aerosol-generating system 400 comprising an aerosol-generating article 301 according to the present invention. The aerosol-generating article 301 is substantially the same as the aerosol-generating article 201 described with reference to FIG. 3, but with the addition of a mouthpiece 402 attached to an end of the first tube 104 and an aluminium heat transfer element 404 attached to an end of the second tube 102. The aerosol-generating system 400 further comprises an aerosol-generating device 406 into which the aerosol-generating article 301 is received. The aerosol-generating device 406 comprises a heater 408 for heating the rupturing system 200 via the heat transfer element 404 when the rupturing system 200 has been moved into the second position shown in FIG. 5 to release the volatile liquids from the blister capsules 210, 212.

The invention claimed is:

1. An aerosol-generating article comprising at least one blister capsule comprising a volatile liquid, the aerosol-generating article further comprising a rupturing system, the rupturing system comprising:

a first tube and a second tube both being arranged in operational engagement defining a volume, wherein the first tube and the second tube are movable relative to each other along a first motion path from a first position to a second position, such that the defined volume is larger in the first position than in the second position, wherein the first tube comprises a first rupturing member arranged at least partially inside the first tube, such that in the first position the first rupturing member is contained completely in the defined volume of the first tube and the second tube, and wherein in the second position, the first rupturing member at least partially protrudes from the defined volume and is configured to rupture the at least one blister capsule and to form an aperture extending through the at least one blister capsule.

2. The aerosol-generating article according to claim 1, wherein the first rupturing member comprises a distal end comprising a rupturing portion and a proximal end, and wherein the first rupturing member is coupled to the first tube at the proximal end such that during movement of the first tube along the first motion path, the rupturing portion describes a second motion path that is at least partially not parallel to the first motion path.

3. The aerosol-generating article according to claim 2, wherein the second tube comprises a guide member configured to guide the rupturing portion of the first rupturing member along the second motion path.

4. The aerosol-generating article according to claim 3, wherein the guide member comprises a cam surface and the first rupturing member comprises a cam follower surface, such that during relative movement of the first tube and the second tube from the first position to the second position along the first motion path, the cam follower surface of the first rupturing element engages with the cam surface of the guide member to guide the rupturing portion of the first rupturing member along the second motion path.

5. The aerosol-generating article according to claim 3, wherein the at least one blister capsule comprises a first blister capsule and a second blister capsule, wherein the guide member is a second rupturing member arranged at least partially inside the second tube such that in the first position the second rupturing member is contained completely in the defined volume of the first tube and the second tube, and wherein in the second position the first rupturing member at least partially protrudes from the defined volume and is configured to rupture the first blister capsule to form an aperture extending through the first blister capsule, and the second rupturing member at least partially protrudes from the defined volume and is configured to rupture the second blister capsule to form an aperture extending through the second blister capsule.

6. The aerosol-generating article according to claim 5, wherein the second rupturing member comprises a distal end comprising a rupturing portion and a proximal end, and wherein the second rupturing member is connected to the second tube at the proximal end such that during movement of the second tube along the first motion path, the rupturing portion describes a third motion path that is at least partially not parallel to the first motion path.

7. The aerosol-generating article according to claim 5, wherein each of the first rupturing member and the second rupturing member is coupled to a respective tube of the first tube and the second tube by a resilient member.

8. The aerosol-generating article according to claim 1, wherein the first tube and the second tube are substantially hollow, and wherein an engagement surface of the first tube is configured to slide adjacent an engagement surface of the second tube.

9. The aerosol-generating article according to claim 8, wherein the engagement surface of the first tube and the engagement surface of the second tube each comprise one or more resilient protrusions configured to cooperate to retain the rupturing system in the first position until a compressive force is applied to the aerosol-generating article along the first motion path.

10. The aerosol-generating article according to claim 8, wherein the engagement surface of the first tube and the engagement surface of the second tube each comprise one or more resilient protrusions configured to cooperate to retain the rupturing system in the second position.

11. The aerosol-generating article according to claim 8, wherein one of the first tube and the second tube comprises a shoulder, the aerosol-generating article further comprising a removable tab positioned adjacent the shoulder and between the first tube and second tube and being configured to prevent the first tube and second tube from moving from the first position to the second position.

12. The aerosol-generating article according to claim 1, wherein the second tube comprises a first end and a second end, wherein the first tube overlaps the first end of the second tube in the first position, wherein the at least one blister capsule is connected to the second end of the second tube, and wherein in the second position the first rupturing member ruptures the at least one blister capsule connected to the second end of the second tube.

13. The aerosol-generating article according to claim 1, wherein the at least one blister capsule further comprises:
a blister shell,
a tubular porous element disposed in the blister shell, the volatile liquid sorbed on the tubular porous element, and
a film configured to seal the blister shell, and
wherein the film and the blister shell are frangible such that, in the second position, the first rupturing member at least partially protrudes from the defined volume and is configured to rupture the film and the blister shell of the at least one blister capsule.

14. The aerosol-generating article according to claim 1, further comprising a mouthpiece element adjacent to one of the first tube or second tube.

15. The aerosol-generating article according to claim 1, further comprising at least one heater configured to heat the volatile liquid within the at least one blister capsule to form an aerosol.

* * * * *